United States Patent
Truong et al.

(10) Patent No.: US 10,352,755 B2
(45) Date of Patent: Jul. 16, 2019

(54) PASSIVE DIFFERENTIAL LIQUID LEVEL SENSOR USING OPTICAL FIBERS

(71) Applicant: The Boeing Company, Chicago, IL (US)

(72) Inventors: Tuong K. Truong, Bellevue, WA (US); Dennis G. Koshinz, Bellevue, WA (US); Eric Y. Chan, Mercer Island, WA (US); Kim Quan Anh Nguyen, Seattle, WA (US)

(73) Assignee: The Boeing Company, Chicago, IL (US)

(*) Notice: Subject to any disclaimer, the term of this patent is extended or adjusted under 35 U.S.C. 154(b) by 146 days.

(21) Appl. No.: 15/489,066

(22) Filed: Apr. 17, 2017

(65) Prior Publication Data
US 2018/0299318 A1    Oct. 18, 2018

(51) Int. Cl.
G01F 23/292 (2006.01)
G01N 9/00 (2006.01)
G01G 9/00 (2006.01)
B64D 37/00 (2006.01)

(52) U.S. Cl.
CPC ....... G01F 23/2925 (2013.01); B64D 37/005 (2013.01); G01F 23/292 (2013.01); G01G 9/00 (2013.01); G01N 9/00 (2013.01)

(58) Field of Classification Search
CPC .................. G01F 23/292; G01N 9/24
See application file for complete search history.

(56) References Cited

U.S. PATENT DOCUMENTS

| 4,870,292 A | 9/1989 | Alpert et al. |
| 4,928,006 A | 5/1990 | Kershaw |
| 4,942,306 A | 7/1990 | Colbourne |
| 4,994,682 A | 2/1991 | Woodside |
| 6,172,377 B1 | 1/2001 | Weiss |

(Continued)

FOREIGN PATENT DOCUMENTS

| CA | 1332205 | 10/1994 |
| DE | 3940455 A1 | 9/1990 |

(Continued)

OTHER PUBLICATIONS

Extended European Search Report dated Aug. 18, 2018 in European Application No. 18163932.9 (European counterpart of the instant patent application).

(Continued)

Primary Examiner — Peter J Macchiarolo
Assistant Examiner — Alexander A Mercado
(74) Attorney, Agent, or Firm — Ostrager Chong Flaherty & Broitman P.C.

(57) ABSTRACT

Systems and methods that use a passive differential optical sensor to measure the level of liquid in a reservoir (e.g., a fuel tank or other storage container). More specifically, the passive differential optical liquid level sensor solves the problem of common-mode intensity variations by employing three optical fibers that will be disposed vertically in the reservoir. The system comprises a side-emitting optical fiber having one end optically coupled to an optical source, a side-receiving optical fiber optically coupled to a first optical detector, and a total internal reflection optical fiber having one end optically coupled to the other end of the side-emitting optical fiber and another end optically coupled to a second optical detector. A computer or processor is configured to perform differential processing of the detected light and then determine the liquid level based on the differential processing results.

15 Claims, 6 Drawing Sheets

(56) References Cited

U.S. PATENT DOCUMENTS

| | | |
|---|---|---|
| 6,274,880 B1 | 8/2001 | Walker |
| 6,333,512 B1 | 12/2001 | Wirthlin |
| 6,429,447 B1 | 8/2002 | Nowak et al. |
| 6,795,598 B1 | 9/2004 | Devenyi |
| 7,049,622 B1 | 5/2006 | Weiss |
| 7,161,165 B2 | 1/2007 | Wirthlin |
| 7,660,494 B2 | 2/2010 | Anderson |
| 7,710,567 B1 | 5/2010 | Mentzer et al. |
| 2005/0236591 A1 | 10/2005 | Wirthlin |
| 2007/0145309 A1 | 6/2007 | Zhang |
| 2009/0076744 A1 | 3/2009 | Anderson |
| 2009/0084995 A1 | 4/2009 | Cierullies et al. |
| 2014/0014777 A1 | 1/2014 | Kreitmair-Steck et al. |
| 2015/0100253 A1 | 4/2015 | Austerlitz et al. |
| 2016/0138958 A1 | 5/2016 | Truong et al. |

FOREIGN PATENT DOCUMENTS

| | | |
|---|---|---|
| EP | 2330393 A1 | 6/2011 |
| GB | 2293007 A | 3/1996 |
| WO | 2010051806 A1 | 5/2010 |

OTHER PUBLICATIONS

Abstract, Zhao et al., "Novel light-leaking optical fiber liquid-level sensor for aircraft fuel gauging", Opt. Eng., vol. 52, No. 1, 014402 (Jan. 4, 2013); http://dx.doi.org/10.1117/1.OE.52.1.014402.
English Abstract of DE3940455.

PASSIVE DIFFERENTIAL LIQUID LEVEL SENSOR USING OPTICAL FIBERS

BACKGROUND

This disclosure generally relates to systems and methods for measuring a level of liquid in a reservoir, such as a storage tank or other container. More particularly, this disclosure relates to systems and methods for liquid level measurement using an optical sensor.

The level of a liquid is continuously measured in many commercial and military applications. For example, liquid-level sensors are commonly used in the fuel tanks of airplane, automobiles, and trucks. Liquid-level sensors are also used to monitor liquid levels within storage tanks used for fuel dispensing, wastewater treatment, chemical storage, food processing, etc.

Many transducers for measuring liquid level employ electricity. The electrical output of such transducers changes in response to a change in the liquid level being measured, and is typically in the form of a change in resistance, capacitance, current flow, magnetic field, frequency, and so on. These types of transducers may include variable capacitors or resistors, optical components, Hall Effect sensors, strain gauges, ultrasonic devices, and so on.

Currently most fuel sensors on airplane use electricity. For example, existing electrical capacitance sensors require electrical wiring inside the tank, which in turn requires complex installations and protection measures to preclude a safety issue under certain electrical fault conditions. This electrical wiring requires careful shielding, bonding, and grounding to minimize stray capacitance and further requires periodic maintenance to ensure electrical contact integrity.

A simplex (non-differential) optical impedance fuel level sensor based on optical intensity measurement has been proposed which would eliminate all electrical elements. One such optical impedance fuel level sensor comprises two optical fibers spaced apart inside a meniscus tube: a side-emitting optical fiber that transmits light along its length and a side-receiving optical fiber that receives emitted light along its length. The meniscus tube minimizes the sloshing of fuel level. The variable fuel level in the tank produces changes in the optical impedance between the two optical fibers, resulting in changes in the total light received by an optical detector.

However, the aforementioned simplex optical impedance fuel level sensor is susceptible to inaccuracy due to intensity variations along the optical path that are not related to fuel level. These intensity variations may be attributable to one or more of the following factors: (1) temperature variation; (2) surface tension wetting (non-shedding of liquid); (3) fuel gunk buildup on the optical window surface of the fiber sensor elements; (4) ice slush in the lower portion of the fuel tank due to water condensation and cold temperature; (5) fuel surface tilt in a dynamic flight environment; (6) fiber attenuation due to aging; (7) fiber attenuation due to bending; (8) connector attenuation due to alignment; (9) non-uniformity of light emitting along the length of the side-emitting optical fiber due to manufacturing imperfection; and (10) non-uniformity of light received along the length of the side-receiving optical fiber due to manufacturing imperfection.

It would be desirable to provide an optical liquid level sensor that that is not afflicted with one or more of the aforementioned sources of intensity variation.

SUMMARY

The subject matter disclosed herein is directed to improvements in systems and methods that use a passive differential optical sensor to measure the level of liquid in a reservoir (e.g., a fuel tank or other storage container). More specifically, the passive differential optical liquid level sensor disclosed in some detail below solves the problem of common-mode intensity variations by employing three optical fibers that will be disposed vertically in the reservoir. The system comprises a side-emitting optical fiber having one end optically coupled to an optical source, a side-receiving optical fiber optically coupled to a first optical detector, and a total internal reflection optical fiber having one end optically coupled to the other end of the side-emitting optical fiber and another end optically coupled to a second optical detector. A computer or processor is configured to perform differential processing of the light impinging on the first and second optical detectors and determine the liquid level based on the differential processing results.

During operation, the side-emitting optical fiber emits some of the received light along its length toward a side-receiving optical fiber. The side-emitting and side-receiving optical fibers are disposed in parallel and spaced apart inside a meniscus tube. The meniscus tube minimizes the sloshing of fuel level. The side-receiving fiber is used to sense the level of liquid in the reservoir. Some of the side-emitted light received along the length of the side-receiving optical fiber exits the upper end of the side-receiving optical fiber and impinges on the first optical detector. The variable liquid level in the reservoir produces changes in the optical impedance between the two optical fibers (i.e., modulates the optical power between the side-emitting fiber and the side-receiving fiber), resulting in changes in the total light (i.e., optical power) received by the first optical detector.

The total internal reflection optical fiber is used as a reference to subtract out the common-mode intensity variations that can affect the liquid level readings (such as LED aging, fiber aging, fuel gunk and temperature). By subtracting the optical power output by the total internal reflection optical fiber from the optical power output by the side-receiving optical fiber, common-mode intensity variations can be neutralized, thereby enhancing the accuracy of the received optical power reading and the resulting liquid level indication. Depending on the height of the reservoir, which can range from a few inches to a few feet, this differential optical sensor has different apparatuses that shape the light to be unidirectional (emitted and collected only on one side of the fiber) or omnidirectional (all directions). The fiber can be either glass or plastic with sufficient optical output along the entire length of the sensor.

As used herein, the phrase "total internal reflection" refers to the phenomenon which occurs when a ray of light is incident on a medium boundary at an angle larger than a particular critical angle with respect to the normal to the surface. If the refractive index is lower on the other side of the boundary and the angle of incidence is greater than the critical angle, the wave cannot pass through and is entirely reflected. The critical angle is the angle of incidence above which the total internal reflection occurs. As used herein, the term "total internal reflection optical fiber" refers to an optical fiber in which all (or substantially all in the event of expected optical losses) of the light entering one end reaches the other end due to the phenomenon of total internal reflection at the core-cladding interface of the optical fiber.

In other words, the total internal reflection optical fiber disclosed hereinbelow is designed to not emit light sideways along its length.

Although various embodiments of systems and methods for optically measuring the level of liquid in a reservoir will be described in some detail below, one or more of those embodiments may be characterized by one or more of the following aspects.

One aspect of the subject matter disclosed in detail below is a system for measuring a level of liquid in a reservoir (e.g., fuel in a fuel tank of an airplane), comprising: an optical source configured to convert input electrical power to output light; a first optical detector configured to convert impinging light into electrical signals having an amplitude which is a function of a first optical power of the light impinging on the first optical detector; a second optical detector configured to convert impinging light into electrical signals having an amplitude which is a function of a second optical power of the light impinging on the second optical detector; a side-emitting optical fiber having one end optically coupled to the optical source and having another end; a side-receiving optical fiber that is positioned parallel to and at a distance from the side-emitting optical fiber and has one end optically coupled to the first optical detector; and a total internal reflection optical fiber having one end optically coupled to the second optical detector and another end optically coupled to the another end of the side-emitting optical fiber. In accordance some embodiment, the foregoing system further comprises a computer system configured to calculate an estimated level of liquid in the reservoir based on a difference of the first and second electrical signals output by the first and second optical detectors. In that case, the system further comprises a display device electrically coupled to the computing system, wherein the computing system is further configured to execute the following operations: storing data representing a geometry of the reservoir; receiving data representing a measurement of a density of the liquid in the reservoir; calculating a mass of liquid remaining in the reservoir based on the geometry of the reservoir, the density of the liquid and the estimated level of liquid; and outputting an electrical signal representing the calculated mass of liquid in the reservoir to the display device.

Another aspect of the subject matter disclosed in detail below is a fuel storage system comprising: a fuel tank having a geometry that defines a volume; a meniscus tube disposed within the volume defined by the geometry of the fuel tank; a first side-emitting optical fiber having one end and another end; a side-receiving optical fiber that is positioned parallel to and at a distance from the first side-emitting optical fiber and has one end and another end; and a first total internal reflection optical fiber having one end and having another end optically coupled to the another end of the first side-emitting optical fiber, wherein the first side-emitting optical fiber, the side-receiving optical fiber and the first total internal reflection optical fiber are disposed within the meniscus tube. In accordance with some embodiments, this system further comprises: an optical source configured to convert input electrical power to output light, wherein the optical source is optically coupled to the one end of the first side-emitting optical fiber; a first optical detector configured to convert impinging light into electrical signals having an amplitude which is a function of a first optical power of the light impinging on the first optical detector, wherein the first optical detector is optically coupled to the one end of the side-receiving optical fiber; and a second optical detector configured to convert impinging light into electrical signals having an amplitude which is a function of a second optical power of the light impinging on the second optical detector, wherein the second optical detector is optically coupled to the one end of the first total internal reflection optical fiber. In accordance with one embodiment, the system further comprises: a computer system configured to calculate an estimated level of fuel in the fuel tank based on a difference of the first and second electrical signals output by the first and second optical detectors; a display device electrically coupled to the computing system; and a densitometer located in the fuel tank and configured to measure a density of fuel in the fuel tank. In this embodiment, the computing system is further configured to execute the following operations: storing data representing the geometry of the fuel tank; receiving data from the densitometer representing a measurement of a density of the fuel in the fuel tank; calculating a mass of fuel remaining in the fuel tank based on the geometry of the fuel tank, the density of the fuel and the estimated level of fuel; and outputting an electrical signal representing the calculated mass of fuel in the fuel tank to the display device.

A further aspect of the subject matter disclosed in detail below is a method for measuring a height of liquid in a reservoir (e.g., fuel in a fuel tank of an airplane), comprising: optically coupling one end of a side-emitting optical fiber to one end of a total internal reflection optical fiber; placing the optically coupled side-emitting and total internal reflection optical fibers in the reservoir; placing a side-receiving optical fiber in the reservoir at a location whereat the side-emitting optical fiber and side-receiving optical fiber are mutually parallel and separated by a distance; outputting light from an optical source; guiding the outputted light into another end of the side-emitting optical fiber; side-emitting at least some of the light propagating in the side-emitting optical fiber toward the side-receiving optical fiber; guiding at least some of the light received by the side-receiving optical fiber onto a first optical detector; guiding at least some of the light received by the total internal reflection optical fiber onto a second optical detector; converting light that impinges on the first optical detector into first electrical signals; converting light that impinges on the second optical detector into second electrical signals; and calculating an estimated level of liquid in the reservoir based on a difference of the first and second electrical signals. In accordance with some embodiments, this method further comprises: storing data representing a geometry of the reservoir; measuring a density of the liquid in the reservoir; calculating a mass of liquid remaining in the reservoir based on the geometry of the reservoir, the density of the liquid and the estimated level of liquid; and displaying a gauge that indicates the calculated mass of liquid in the reservoir. In accordance with one embodiment, the method further comprises acquiring data samples by filling the reservoir with various levels of liquid at different times and then recording the resulting differences between respective sets of first and second electrical signals output by the first and second optical detectors respectively.

Other aspects of differential optical liquid level sensors suitable for use in reservoirs (such as fuel tanks) are disclosed and claimed below.

BRIEF DESCRIPTION OF THE DRAWINGS

The features, functions and advantages discussed in the preceding section can be achieved independently in various embodiments or may be combined in yet other embodiments. Various embodiments will be hereinafter described with reference to drawings for the purpose of illustrating the above-described and other aspects.

Reference will hereinafter be made to the drawings in which similar elements in different drawings bear the same reference numerals.

DETAILED DESCRIPTION

Various embodiments of systems and methods for differential optical measurement of a level of liquid in a reservoir will now be described in detail for the purpose of illustration. At least some of the details disclosed below relate to optional features or aspects, which in some applications may be omitted without departing from the scope of the claims appended hereto. The disclosed differential optical liquid level sensor has application in the measurement of the liquid level in a reservoir onboard a vehicle (such as a fuel tank onboard an airplane) or in other types of liquid storage containers, including standing structures. Fuel tanks and other liquid storage containers are collectively referred to herein as "reservoirs".

In particular, illustrative embodiments of a differential optical fuel level sensor on an airplane are described in some detail below. However, not all features of an actual implementation are described in this specification. A person skilled in the art will appreciate that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Figure 1:
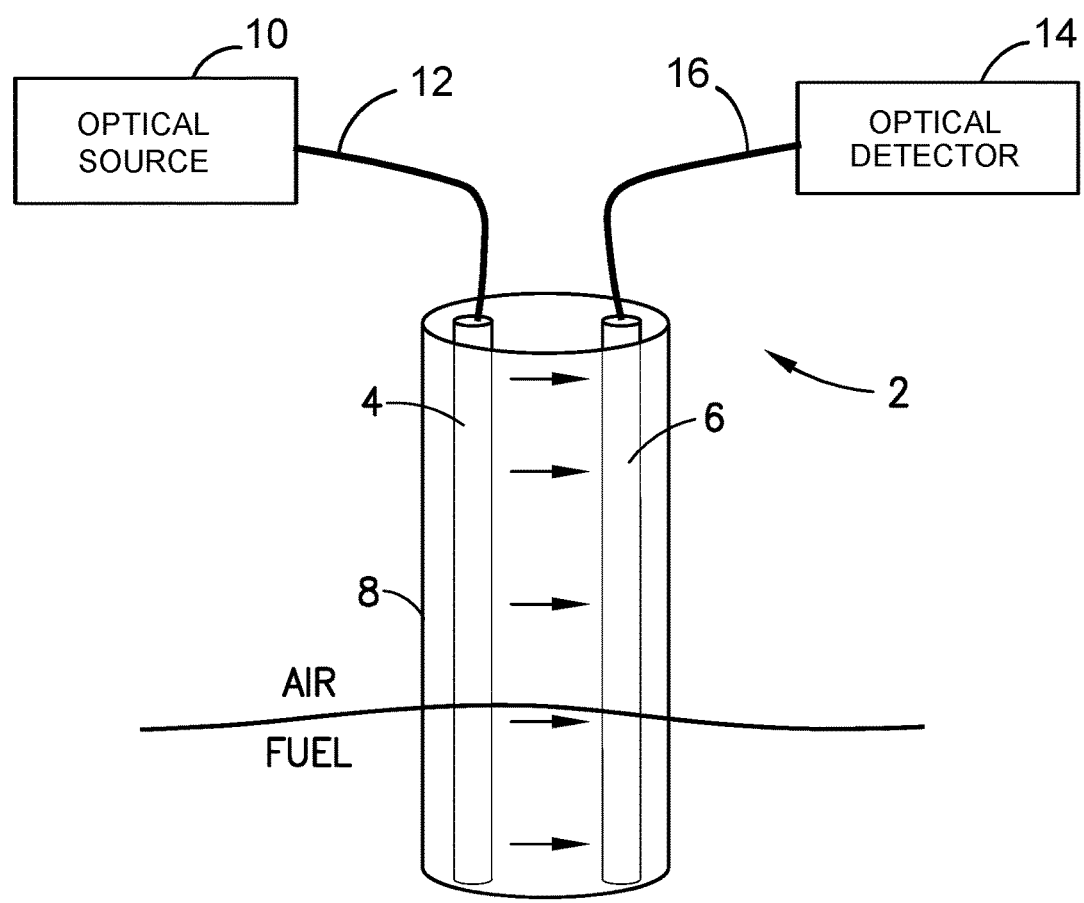
FIG. 1 is a hybrid diagram representing a system for measuring a level of a liquid comprising an optical impedance sensor that detects modulations in the optical impedance of the liquid. This hybrid diagram comprises a block diagram showing components of an optical transceiver and a diagram representing an isometric view of the optical impedance sensor. The nonlinear line spanning the sensor represents a level of liquid; the arrows represent photons propagating from one optical fiber to another optical fiber.

FIG. 1 is a hybrid diagram representing a system for measuring a level of fuel in a reservoir in accordance with the optical impedance modulation concept. The system depicted in FIG. 1 comprises an optical impedance sensor 2 that detects the optical impedance of the fluid separating a side-emitting optical fiber 4 and a side-receiving optical fiber 6, obtaining optical power data that can be later used to determine the fuel level. In accordance with the embodiment shown in FIG. 2, the side-emitting optical fiber 4 is optically coupled to an optical source 10 (e.g., a laser or a light-emitting diode (LED)) by means of an optical fiber 12; and the side-receiving optical fiber 6 is optically coupled to an optical detector 14 (e.g., a photodiode) by means of an optical fiber 16.

The optical impedance sensor 2 further comprises a meniscus tube 8 that minimizes fuel sloshing in a fuel tank (not shown). The nonlinear line spanning the optical impedance sensor 2 in FIG. 1 represents a level of fuel. The side-emitting and side-receiving optical fibers 4 and 6 are placed inside the meniscus tube 8 in spaced-apart relationship (preferably the fibers are straight and parallel to each other). In cases where the fuel tank is incorporated in a wing of an airplane, the side-emitting and side-receiving optical fibers 4 and 6 are preferably rigidly supported in a fixed spatial relationship to provide a separation distance d which is optimized for optical received power versus ice slush particles that may form in the fuel tank. The meniscus tube 8, which extends to the floor of the fuel tank, has openings near that floor which allow fuel to flow into the volume of space bounded by the meniscus tube 8. The level of the fuel will be the same inside and outside the meniscus tube 8.

When pumped by the optical source 10, the side-emitting optical fiber 4 emits light radially outward and toward the side-receiving optical fiber 6. The axial distribution of emitted light may be substantially constant along the length of side-emitting optical fiber 4. A first portion of the light will pass through the fuel and illuminates a lower portion of the side-receiving optical fiber 6. A second portion of light emitted by side-emitting optical fiber 4 will pass through the air and illuminate an upper portion of the side-receiving optical fiber 6. At least some of the light received by side-receiving optical fiber 6 is guided upwards and other light is guided downwards inside the core of side-receiving optical fiber 6. The light guided downwards may be reflected upwards by a mirror (not shown in FIG. 1) disposed at the bottom end of side-receiving optical fiber 6. The light is guided upwards and exits the upper end of side-receiving optical fiber 6. The light output by side-receiving optical fiber 6 is guided by optical fiber 16 to the optical detector 14, which converts impinging light into electrical current. This electrical current is conducted by a cable to a computer or processor (not shown in FIG. 1). The computer or processor is configured to analyze the optical power data acquired from the optical detector 14 and compute the height h of the air/fuel interface. As will be explained in more detail below, the computer or processor may also be configured to receive fuel temperature data from a temperature sensor during refueling and to receive fuel density data from a densitometer and compute the quantity of fuel in the fuel tank based on the optical power, fuel density data and known geometry of the fuel tank (or compartment thereof) during flight. In this case, the computer may be referred to as a fuel quantity processing unit (FQPU).

The arrows in FIG. 1 represent light (i.e., photons) propagating from the side-emitting optical fiber 4 to the side-receiving optical fiber 6 during operation of optical source 10. During monitoring of the fuel level, the brightness (i.e., intensity) of the light produced by optical source 10 (i.e., its optical power) is preferably constant. As the fuel level varies, the optical impedance of the fuel in the volume of space between side-emitting optical fiber 4 and side-receiving optical fiber 6 changes in dependence on the fuel level, due to the fact that air and fuel have different refractive indices.

It is well known that air has an index of refraction less than the index of refraction of fuel; that fuel has an index of refraction less than the index of refraction of cladding of an optical fiber; and that the cladding has an index of refraction less than the index of refraction of the core of the optical fiber. The refractive indices determine the amount of light that is reflected when reaching an interface.

Since more optical power is lost (i.e., optical impedance is greater) in liquids than in air, the optical power output by the side-receiving optical fiber 6 will monotonically increase as the liquid level falls. In other words, as the fuel level changes, the optical impedance between side-emitting optical fiber 4 and side-receiving optical fiber 6 will change. These changes in optical impedance in turn produce changes in the optical power (i.e., light intensity) output by the side-receiving optical fiber 6 to the optical detector 14.

Although not depicted in FIG. 1, each optical fiber is a flexible, optically transparent or translucent fiber made of extruded glass or plastic. It can function as a waveguide or light pipe to transmit light between the two ends of the fiber. The term "optical fiber" as used herein refers to a cylindrical dielectric waveguide that transmits light along its axis. The fiber consists of a transparent core surrounded by a transparent cladding layer (hereinafter "cladding"), both of which are made of dielectric materials. Light is kept in the core by the phenomenon of total internal reflection. To confine the optical signal in the core, the refractive index of the core is greater than that of the cladding. The boundary between the core and cladding may either be abrupt, as in step-index fiber, or gradual, as in graded-index fiber. The embodiments disclosed herein employ plastic optical fibers. Plastic optical fibers have high transmission capacity, excellent immunity to electromagnetic interference-induced noise, light weight, high mechanical strength, and outstanding flexibility. Plastic optical fibers are also larger in diameter as compared to glass optical fibers. Due to their larger diameters, plastic optical fibers have greater tolerance for fiber misalignment than glass optical fibers have. Because of this large misalignment tolerance, plastic optical fiber-based networks have lower maintenance and installation costs. In aerospace platforms, plastic optical fibers also greatly reduce the cost of connectors and transceiver components used in an avionics network. In alternative embodiments, glass optical fibers can be used in place of plastic optical fibers.

The systems and methods disclosed herein also utilize side-emitting optical fibers. The side-emitting optical fibers utilized herein have a plastic or glass core clad with a material that is different than the material of the core. To enable side emission, scattering features are introduced into the optical fiber at various locations. In accordance with one method, the core region is doped with small refractive and/or reflective light-scattering particles during manufacture. Alternatively, the surface of the core is modified or treated to have surface features that scatter light out of the core. Some examples of light-emitting surface features include serrations, notches, scratches, texture, roughness, corrugations, etching, abrasion, etc. For example, the cladding of the side-emitting optical fiber can be modified by roughening it to enable a controlled level of light output along the fiber's length. The entire length of fiber can be modified or treated to have side-emitting properties, or just a portion of the fiber (i.e., a portion along the length or circumference of the fiber, or both). Side-emitting optical fibers also inherently function in reverse, i.e., as "side-receiving" optical fibers, because the same features that scatter light out of the optical fiber (i.e., when illuminated from one end) can also scatter light into the optical fiber (i.e., when illuminated from the side). However, although in theory a side-emitting optical fiber also qualifies as a side-receiving optical fiber, as used herein the term "side-emitting optical fiber" will be used to refer to an optical fiber that receives light at one end and emits at least some of that light from the side, while the term "side-receiving optical fiber" will be used to refer to an optical fiber that receives light from the side and emits at least some of that light from one end.

In accordance with the embodiments disclosed herein, the cladding of the side-emitting optical fiber 4 is modified (e.g., by roughening or notching the circumferential surface) to enable a controlled level of radial light output along the fiber's length. More specifically, the cladding of side-emitting optical fiber 4 may be treated to produce a non-uniform surface at least in an area bounded by a longitudinal slot in a jacket. For example, the outer surface of the cladding may be roughened or notched at least in an area overlapped by a longitudinal slot in a jacket, thereby forming a side window, as will be described in more detail below with reference to FIGS. 5 and 6. The cladding of the side-receiving optical fiber 6 may be modified in a similar manner to form a side window that faces toward the side window of the side-emitting optical fiber 4 when the optical sensor is installed inside a fuel tank.

In addition or in the alternative, the side-receiving optical fiber 6 can be a fluorescent fiber having a core containing fluorescing dopants, which can be activated by light from the side-emitting optical fiber 4 impinging on the side window of the side-receiving optical fiber 6 and then entering the core of the side-receiving optical fiber 6. (Fluorescence occurs when an orbital electron relaxes to its ground state by emitting a photon of light after being excited to a higher quantum state by some type of energy.) The fluorescing dopants produce light which travels along the length of the side-receiving optical fiber 6 and is then output to the optical detector 14.

At any given axial position along the length of the side-emitting optical fiber 4, the circumferential variation in the emitted light is preferably strongly peaked in a narrow angular range subtended by the side window formed by modification of the cladding of the side-emitting optical fiber 4. As previously mentioned, this side window can be formed by modifying the cladding of the optical fibers (e.g., by notching, scratching or sanding) on only one side to more easily emit light with an angular spread that impinges on a corresponding side window formed by modification of the cladding of the side-receiving optical fiber 6.

Figure 2:
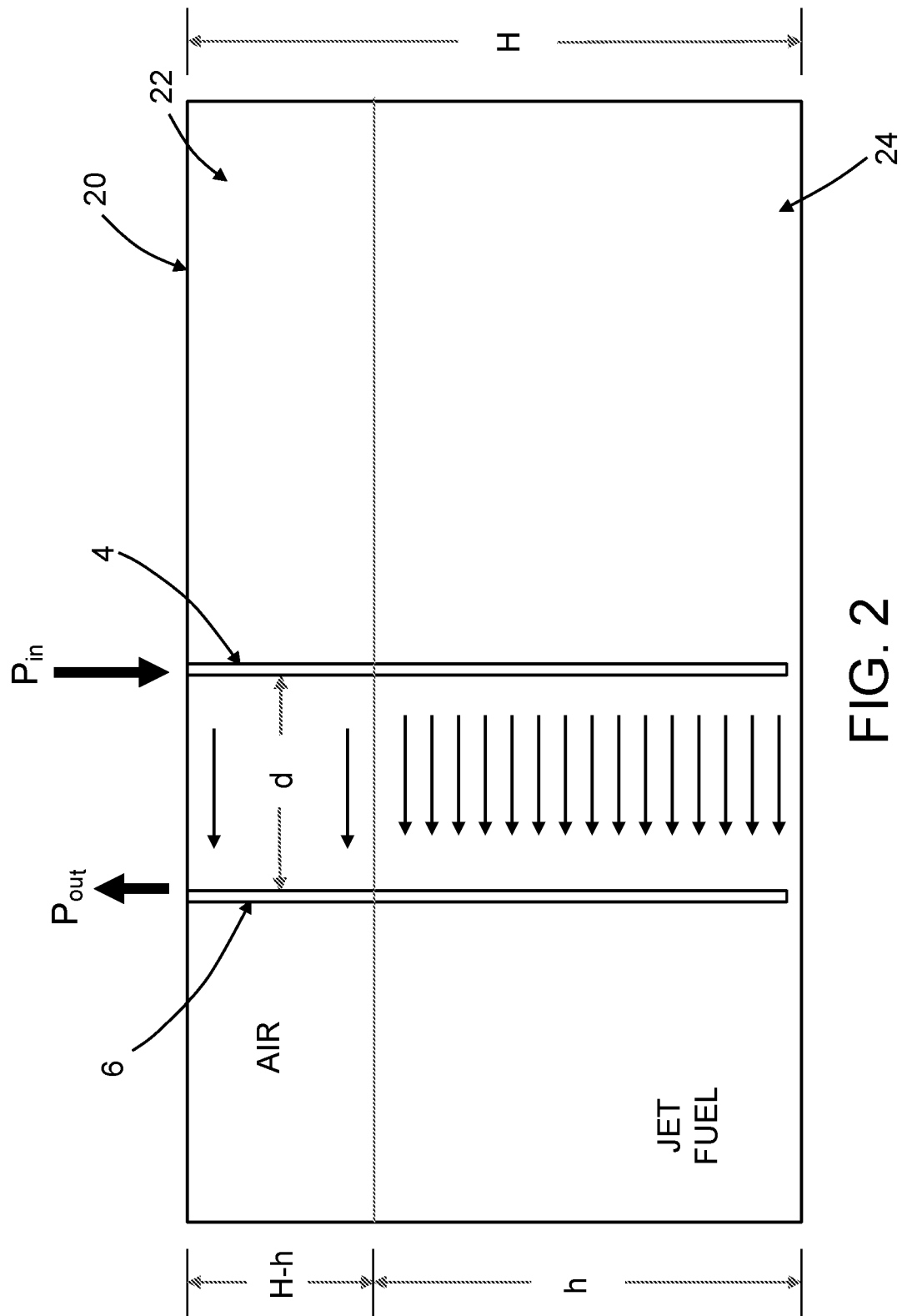
FIG. 2 is a diagram representing a side-emitting optical fiber and a side-receiving optical fiber separated by a distance d inside a fuel tank.

The theoretical underpinning of the optical impedance fuel level sensor concept will now be described with reference to FIG. 2, which shows a side-emitting optical fiber 4 and a side-receiving optical fiber 6 separated by a distance d inside a fuel tank 20 that is partly filled with fuel 24. A typical diameter of side-emitting optical fiber 4 and side-receiving optical fiber 6 is 1 mm. In the configuration depicted in FIG. 2, light from a light source (not shown), having an input optical power $P_{in}$, is input to the side-emitting optical fiber 4. The horizontal arrows in FIG. 2 represent the propagation of side-emitted light from side-emitting optical fiber 4. The light output from the side-receiving optical fiber 6 has an output optical power $P_{out}$ that is highest when the fuel tank 20 is empty. As the fuel level rises, the output optical power $P_{out}$ decreases. By measuring the change in $P_{out}$, the fuel level change can be derived.

In the example shown in FIG. 2, optical fibers are used to measure the level of fuel in a fuel tank. In other embodiments, the same apparatus may be used to detect other liquids. For example, the system described above may be used to detect the presence of water in a container or hydraulic fluids in a reservoir for a hydraulic system. The illustration of detecting fuel in a fuel tank is presented for purposes of illustration and not meant to limit the manner in which the system shown in FIG. 2 may be used.

In FIG. 2, the following dimensions are indicated: the fuel level is h; and the total length of the side-emitting optical fiber 4 and of the side-receiving optical fiber 6 is set equal to H, since the end faces of the two optical fibers are close to the bottom of the fuel tank 20 and H is close to the height of the fuel tank 20. The relationship of output optical power $P_{out}$ versus fuel level h is a function of the side-emitting efficiency per unit area of the side-emitting optical fiber 4, the photo response efficiency per unit area of the side-receiving optical fiber 6, and other factors. Physically, as the fuel level changes, $P_{out}$ is the summation of the output optical power $P_{out/air}$ due to absorption of photons from the side-emitting optical fiber 4 by the air 22 and the output optical power $P_{out/fuel}$ due to absorption of photons from the side-emitting optical fiber 4 by the fuel 24, i.e., $P_{out} = P_{out/air} + P_{out/fuel}$.

In principle, a single side-emitting optical fiber 4 and a single side-receiving optical fiber 6 should be able to provide the fuel level information based on the detected output optical power $P_{out}$ of the side-receiving optical fiber 6. But in a real airplane fuel tank, there are issues of fuel gunk and residue which can build up on the surfaces of the side-emitting optical fiber and side-receiving optical fiber. This build-up obscures the fuel level (h) measuring accuracy. Another consideration is that the quality of fuel used in an airplane in service can change over time because different countries may provide different grades of fuel at their airports. In addition, the sensor system should have a stable light source (laser or LED) to provide a proper optical power input $P_{in}$ to the side-emitting optical fiber 4 for measuring fuel level h. Also, over time the optical fibers can age and the side-emitting optical fiber emitting efficiency and the side-receiving optical fiber response efficiency can be degraded over time.

Figures 3, 4:
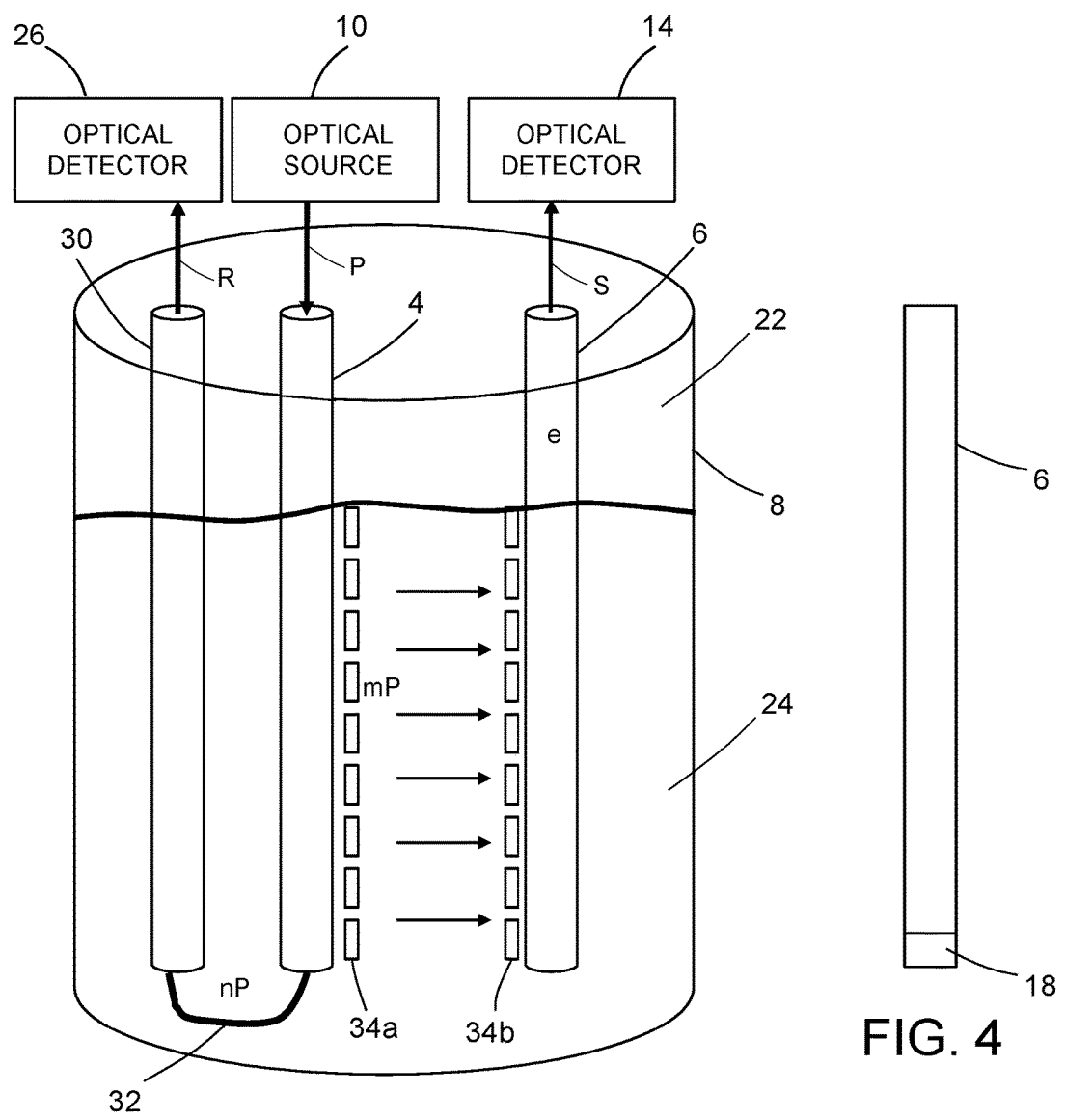
FIG. 3 is a hybrid diagram representing a system for measuring a level of fuel comprising a side-emitting optical fiber optically coupled to an optical source, a side-receiving optical fiber optically coupled to a first optical detector, and a total internal reflection optical fiber optically coupled to one end of the side-emitting optical fiber and a second optical detector.
FIG. 4 is a diagram representing an elevation view of an optical fiber having a mirror cap at one end for increasing the intensity of light exiting the other end of the optical fiber.

To overcome these issues, passive differential optical fuel level sensors of the type proposed herein can be installed in a fuel tank. The passive differential optical liquid level sensor disclosed below solves the problem of common-mode intensity variations by employing three optical fibers that will be disposed vertically in the reservoir. FIG. 3 is a diagram representing a side-emitting optical fiber 4, a side-receiving optical fiber 6 and a total internal reflection optical fiber 30 disposed inside a meniscus tube 8 arranged inside a fuel tank (not shown). These optical fibers are positioned so that the side-receiving optical fiber 6 will receive side-emitted light from the side-emitting optical fiber and the total internal reflection optical fiber 30 will receive end-emitted light from the side-emitting optical fiber. The side-emitting optical fiber 4 is optically coupled to an optical source 10 by a first optical waveguide (not shown in FIG. 3); the side-receiving optical fiber 6 is optically coupled to a first optical detector 14 by a second optical waveguide (not shown in FIG. 3); and the total internal reflection optical fiber 30 is optically coupled to a second optical detector 26 by a third optical waveguide (not shown in FIG. 3). Each optical waveguide may comprise a single length of optical fiber or a plurality of lengths of optical fiber connected in series by optical connectors (not shown in the drawings). The light propagating through the first through third optical waveguides is indicated by respective arrows P, S and R in FIG. 3.

FIG. 3 also depicts one of the factors which may cause common-mode variations in the optical intensity of the light propagating from the side-emitting optical fiber 4 into the side-receiving optical fiber 6, namely, fuel gunk and residue buildup 34a on the external surface of the side window of the side-emitting optical fiber 4 and fuel gunk and residue buildup 34b on the external surface of the side window of the side-receiving optical fiber 6. By computing a difference of the received optical powers output by the side-receiving optical fiber 6 and total internal reflection optical fiber 30, the intensity variations that affect the received power reading and therefore the fuel level accuracy can be neutralized.

In accordance with one proposed implementation, the side-emitting optical fiber 4 and side-receiving optical fiber 6 are disposed in parallel with respective side windows confronting each other across a space that may be at least partially occupied by fuel. Light having an optical power P is input into the upper end of the side-emitting optical fiber 4 from the optical source 10 (which may comprise an LED and an LED driver) by way of an optical waveguide (not shown in FIG. 3) and propagates down the length of the side-emitting optical fiber 4. The lower end of the side-emitting optical fiber 4 is optically coupled to the lower end of the total internal reflection optical fiber 30 by way of an optical waveguide 32. In a preferred embodiment, the side-emitting optical fiber 4, optical waveguide 32 and total internal reflection optical fiber 30 are formed by a single continuous optical fiber, which may be U-shaped.

The side-emitting optical fiber 4 emits a portion of the light having optical power P along its length from its side window, which light propagates through either air 22 or fuel 24 and toward the side window of the side-receiving optical fiber 6. That side-emitted light is indicated by multiple horizontal arrows in FIG. 3. At the instant when side-emitted light exits the side-emitting optical fiber 4, the optical power of that side-emitted light is mP (i.e., the product of m and P), where m is a fractional number between zero and unity representing the proportion of input optical power P which is side-emitted by the side-emitting optical fiber 4. For example, if one half of the received optical power P escapes through the side window of the side-emitting optical fiber 4, then m=½. As the side-emitted light propagates through fuel 24, the optical power mP will diminish, i.e., will become progressively less than the side-emitted optical power mP, due to the optical impedance of the fuel 24. The optical power of the side-emitted light impinging on the side window of the side-receiving optical fiber 6 will be equal to mP/h, where h is the fuel level (i.e., height).

At least some of the side-emitted light that enters the side-receiving fiber 6 will propagate axially along the length of the side-receiving fiber 6 and exit the upper end face with an optical power S which is less than the optical power (mP/h) of the side-emitted light impinging on the side window of the side-receiving optical fiber 6. This optical loss is due to the fact that not all side-emitted light entering the side window of the side-receiving optical fiber 6 is converted into light exiting the upper end face of the side-receiving optical fiber 6. The efficiency of such conversion can be expressed as a parameter e (hereinafter "conversion efficiency e"), which is known for each type of side-receiving optical fiber made of known materials and having a known structure. The conversion efficiency may have any value between zero and unity inclusive. Thus the optical power of the side-emitted light which exits the upper end face of the side-receiving optical fiber 6 (hereinafter "the sensing optical power S") can be expressed by the equation:

$$S=meP/h$$

(i.e., the product of fuel level h, fraction m, conversion efficiency e and input power P).

Referring again to the side-emitting optical fiber 4, the portion of the light having input optical power P received by and not side-emitted by the side-emitting optical fiber 4 has an optical power nP, where n is a fractional number between zero and unity representing the proportion of input optical power P which is end-emitted by the side-emitting optical fiber 4, and where m+n=1 (i.e., P=mP+nP). That portion of the light of optical power nP propagates downward along the length of the side-emitting optical fiber 4 and exits the lower end face of the side-emitting optical fiber 4 (hereinafter "end-emitted light). The lower end face of the side-emitting optical fiber 4 is optically coupled to the lower end face of the total internal reflection optical fiber 30 by way of optical waveguide 32, which may comprise a separate optical fiber. Preferably the side-emitting optical fiber 4, total internal reflection optical fiber 30 and optical waveguide 32 are respective parts of a single continuous optical fiber of constant diameter. The end-emitted light of optical power nP propagates upward along the length of the total internal reflection optical fiber 30 and exits the upper end face of the total internal reflection optical fiber 30. Disregarding optical losses inside the side-emitting optical fiber 4 and the total internal reflection optical fiber 30, the optical power of the end-emitted light exiting the upper end face of the total internal reflection optical fiber 30 (hereinafter "reference optical power R") can be expressed by the following equation:

$$R=nP=P-mP$$

Still referring to FIG. 3, the light (of sensing optical power S) exiting the upper end face of the side-receiving optical fiber 6 is received by a first optical detector 14 by way of one optical waveguide (not shown in FIG. 3), while the light (of reference optical power R) exiting the upper end face of total internal reflection optical fiber 30 is received by a second optical detector 26 by way of another optical waveguide (not shown in FIG. 3). Preferably the optical waveguides comprise respective optical fibers having the same diameters as the diameters of the side-receiving optical fiber 6 and the total internal reflection optical fiber 30 respectively.

When pumped by the optical source 10, the side-emitting optical fiber 4 emits light radially outward and toward the side-receiving optical fiber 6. The axial distribution of emitted light may be substantially constant along the length of side-emitting optical fiber 4. A first portion of the light will pass through the fuel and illuminates a lower portion of the side-receiving optical fiber 6. A second portion of light emitted by side-emitting optical fiber 4 will pass through the air and illuminate an upper portion of the side-receiving optical fiber 6. At least some of the light received by side-receiving optical fiber 6 is guided upwards and other light is guided downwards inside the core of side-receiving optical fiber 6. The light guided downwards may be reflected upwards from a mirror (not shown in FIG. 1, but see mirror 18 in FIG. 4) disposed at the bottom end of side-receiving optical fiber 6. The light is guided upwards and exits the upper end face of side-receiving optical fiber 6. The light output by side-receiving optical fiber 6 impinges on the first optical detector 14, which converts impinging light into electrical current. The fuel level in the tank modulates the optical impedance between the side-emitting optical fiber 4 and the side-receiving optical fiber 6, resulting in changes in total light collected by the first optical detector 14.

At the same time, the light received by the total internal reflection optical fiber 30 is guided upwards inside the core of the total internal reflection optical fiber 30 and exits the upper end face of total internal reflection optical fiber 30. The light output by total internal reflection optical fiber 30 impinges on the second optical detector 26, which also converts impinging light into electrical current. The first and second optical detectors 14 and 26 form a differential receiver that outputs first and second electrical signals to a computer system (not shown in FIG. 3). The computer system is configured to calculate an estimated level of fuel in the fuel tank based on a difference of the first and second electrical signals output by that differential receiver.

In accordance with one embodiment, the electrical currents output by the first and second optical detectors 14 and 26 are output to a computer or processor that is configured to subtract the electrical signal representing sensing optical power S (hereinafter "signal S") from the electrical signal representing reference optical power R (hereinafter "signal R") and then compute the height h of the air/fuel interface. The signal R experiences all common-mode intensity variations due to LED aging, fiber aging, fuel gunk and residue, and temperature, but is not influenced by fuel level. The signal S experiences all of the same common-mode intensity variations and also varies in dependence on the fuel level h. By subtracting signal R from signal S (i.e., S−R), common-mode intensity variations can be neutralized, thereby enhancing the accuracy of the received optical power reading and the resulting liquid level indication. In addition, the optical power difference Δ=S−R is proportional to fuel level h. In accordance with one embodiment, the computer or processor (e.g., an FQPU) is configured to input that optical power difference Δ into a look-up table that associates fuel level values with corresponding optical power difference values. As will be explained in more detail below, the computer or processor may also be configured to receive fuel temperature data from a temperature sensor during refueling and fuel density data from a densitometer and compute the quantity of fuel remaining in the fuel tank based on the measured optical powers, the measured fuel density and the known geometry of the fuel tank during flight.

Before operation of the airplane fuel monitoring system for the first time, each installed differential optical fuel level sensor of the type depicted in FIG. 3 should be calibrated. This differential optical fuel level sensor uses one optical fiber (i.e., side-receiving optical fiber 6) for measurement and another optical fiber (i.e., total internal reflection optical fiber 30) as the reference. During the calibration procedure, data samples are acquired by filling a container with various levels of fuel and then recording the resulting sensor readings S and R. More specifically, the fuel level versus associated output optical powers S and R are measured and recorded, and the associated difference S–R is calculated and recorded for each fuel level. Later, during operation of the airplane fuel monitoring system, the output optical powers S and R are used to indicate the fuel level based on the data from the calibration.

In accordance with one embodiment, during the calibration procedure, electronic digital data representing the fuel levels versus the associated difference S–R is calculated for each fuel level and recorded in a look-up table stored in a non-transitory tangible computer-readable storage medium, such as the non-volatile memory of an fuel quantity processing unit (FPQU). In addition, a linear equation is derived that fits the digital calibration data. This linear equation can be used to interpolate between two stored values in the look-up table when the difference S–R is a value between those two stored values. The relationship of fuel level h versus difference S–R is derived from the measurement data acquired during calibration and stored (as electronic digital data) in the processor's (e.g., FPQU's) memory.

In the design shown in FIG. 3, if acrylic plastic optical fiber is selected, visible wavelengths (e.g., red, green, blue etc.) have less attenuation than infrared and should be chosen. If glass fiber or perfluorinated plastic fiber is selected, invisible infrared wavelengths have less attenuation and should be chosen.

In accordance with an alternative embodiment, the side-receiving optical fiber 6 is a fluorescent optical fiber that collects light along the length of the fiber and transmits other light having a different wavelength to the upper end face of the side-receiving optical fiber 6. Fluorescence is the emission of light by a substance that has absorbed light or other electromagnetic radiation. As used herein, the term "fluorescent optical fiber" means an optical fiber that comprises a core surrounded by cladding, wherein the core is doped with special materials that will produce light (i.e., photons) having a first spectral bandwidth centered at a first wavelength when light having a second spectral bandwidth centered at a second wavelength different than the first wavelength is absorbed by that core. Typically the first wavelength is greater than the second wavelength. In accordance with alternative embodiments, fluorescent glass optical fibers can be used instead of fluorescent plastic optical fiber.

Figure 5:
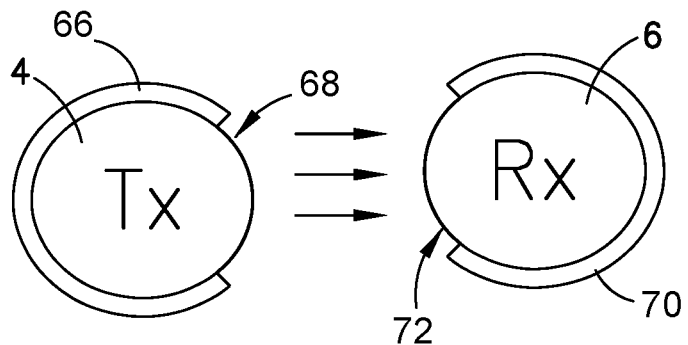
FIG. 5 is a diagram representing a plan view of a pair of optical fibers encased in respective jackets having mutually opposing longitudinal slots for sideways optical coupling of light (indicated by arrows) from the side-emitting optical fiber to the side-receiving optical fiber.

FIG. 5 is a diagram representing a plan view of a pair of straight waveguides of an optical sensor in accordance with an embodiment intended for use in the measurement of a level of a liquid that will not damage exposed optical fibers when the latter are immersed in the liquid. The transmitting waveguide comprises: a side-emitting optical fiber 4 having an axis and a circumferential surface; and a jacket 66 having a longitudinal slot 68 that extends parallel to the axis of the side-emitting optical fiber 4 for the entire length of the latter. Preferably the longitudinal slot 68 overlaps a side window formed by a non-uniform surface on the cladding of the side-emitting optical fiber 4. The jacket 66 is in contact with and covers the circumferential surface of the side-emitting optical fiber 4 except in the area of longitudinal slot 68. The transmitting waveguide may further comprise a curved reflective surface disposed between the side-emitting optical fiber 4 and the jacket 66. Preferably the jacket 66 is made of a material which is not optically transparent or translucent, such as metal or polymeric material.

Similarly, the receiving waveguide comprises: a side-receiving optical fiber 6 having an axis and a circumferential surface; and a jacket 70 having a longitudinal slot 72 that extends parallel to the axis of the side-receiving optical fiber 6 for the entire length of the latter. Preferably the longitudinal slot 72 overlaps the side window formed by a non-uniform surface on the cladding of the side-receiving optical fiber 6. The jacket 70 is in contact with the circumferential surface of the side-receiving optical fiber 6 except in an area of the longitudinal slot 72. The receiving waveguide may further comprise a curved reflective surface disposed between the side-receiving optical fiber 6 and the jacket 70. Preferably the jacket 70 is made of a material which is not optically transparent or translucent, such as metal or polymeric material.

In the case where the jackets 66 and 70 are made of polymeric material, those jackets can be formed by molding. The side-emitting and side-receiving optical fibers may each have a circular, square or hexagonal cross section, with the molded jacket conforming to the shape of the optical fiber. Similarly, the reference waveguide comprises a total internal reflection optical fiber (not shown in FIG. 5) having an axis and a circumferential surface and surrounded by a jacket (without longitudinal slots).

The arrows in FIG. 5 represent light which has been emitted by side-emitting optical fiber 4 through the side window formed in the cladding of the side-emitting optical fiber 4 and is propagating through intervening fluid (e.g., liquid or air) toward the corresponding side window formed in the cladding of side-receiving optical fiber 6. However, it should be appreciated that, in the absence of a focusing lens overlying the side window of the side-emitting optical fiber 4, the exiting rays of light may be divergent, rather than collimated.

Figure 6:
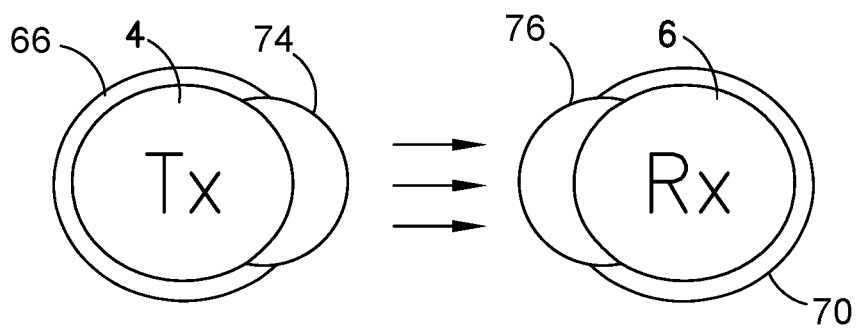
FIG. 6 is a diagram representing a plan view of a pair of optical fibers encased in respective jackets having mutually opposing longitudinal slots covered by respective lenses for sideways optical coupling of light (indicated by arrows) from the side-emitting optical fiber to the side-receiving optical fiber.

FIG. 6 is a diagram representing a plan view of a pair of straight waveguides of an optical sensor in accordance with an embodiment in which the liquid is not in direct contact with the side-emitting and side-receiving optical fibers 4 and 6. The only difference from the embodiment depicted in FIG. 5 is that the transmitting and receiving waveguides further comprise respective lenses 74 and 76 formed (e.g., by molding) in the longitudinal slots of the respective jackets 66 and 70. Preferably the lenses 74 and 76 extend the full length of the longitudinal slots. In combination, lens 74 and jacket 66 encase the side-emitting optical fiber 4, with lens 74 interfacing with the side window of side-emitting optical fiber 4. Similarly, lens 76 and jacket 70 encase the side-receiving optical fiber 6, with lens 76 interfacing with the side window of side-receiving optical fiber 6. Preferably the lenses 74 and 76 are made of epoxy.

The arrows in FIG. 6 represent light which has been emitted by side-emitting optical fiber 4 through the lens 74 and is propagating through intervening fluid (e.g., liquid or air) toward the lens 76 of the receiving waveguide. The lens 74 may be designed so that exiting rays of light are directed in parallel toward the lens 76. The lens 76 may be designed so that impinging parallel rays of light are converged into the side-receiving optical fiber 6. The lenses have the effect of increasing the intensity of the light output by side-receiving optical fiber 6 for the same optical power being pumped into side-emitting optical fiber 4, thereby enhancing the performance of the differential optical sensor.

If the optical power transmitted by a high-intensity LED is adequate, then the system may comprise a single side-emitting optical fiber disposed parallel with one side-receiving optical fiber. If the optical power from one LED is inadequate, then the amount of light emitted can be increased in various ways. In some embodiments, the differential optical liquid level sensor may comprise a single centrally located omnidirectional side-emitting optical fiber surrounded by a multiplicity of side-receiving optical fibers inside a meniscus tube, each of side-receiving optical fibers being partly encased in a respective jacket having a longitudinal slot for sideways reception of light from the side-emitting optical fiber. In this case the entire circumferential surface of the cladding of the side-emitting optical fiber may be modified (e.g., by roughening, notching or sanding) to facilitate the escape of light from the side-emitting optical fiber. During operation, light emitted by the side-emitting optical fibers is directed outward in all directions. The total optical power received by the side-receiving optical fibers will be dependent on the level of liquid inside the meniscus tube. In this case the side-emitting optical fiber is optically coupled to an internal total reflection optical fiber, as described above.

A wing of an airplane has a height that varies, especially in a spanwise direction. As a consequence, a fuel tank incorporated inside an aircraft wing has a height that varies. Typically a wing fuel tank comprises a multiplicity of compartments. It would be desirable to provide different types of fuel level sensors which are suitable for installation in fuel tank compartments of different heights. For example, some compartments at the root of a wing may have a height of a few feet, while other compartments near the tip of the wing may have a height of a few inches.

A tall sensor is typically installed in the fuel tank compartment at the root of the wing. Due to the longer length, there is enough difference in fuel height that enables 1% accuracy by simple use of a straight transmitting optical fiber in parallel with a receiving optical fiber. There is a controlled gap between the two fibers optimized for optical received power versus ice slush particles in the fuel tank.

Figure 7:
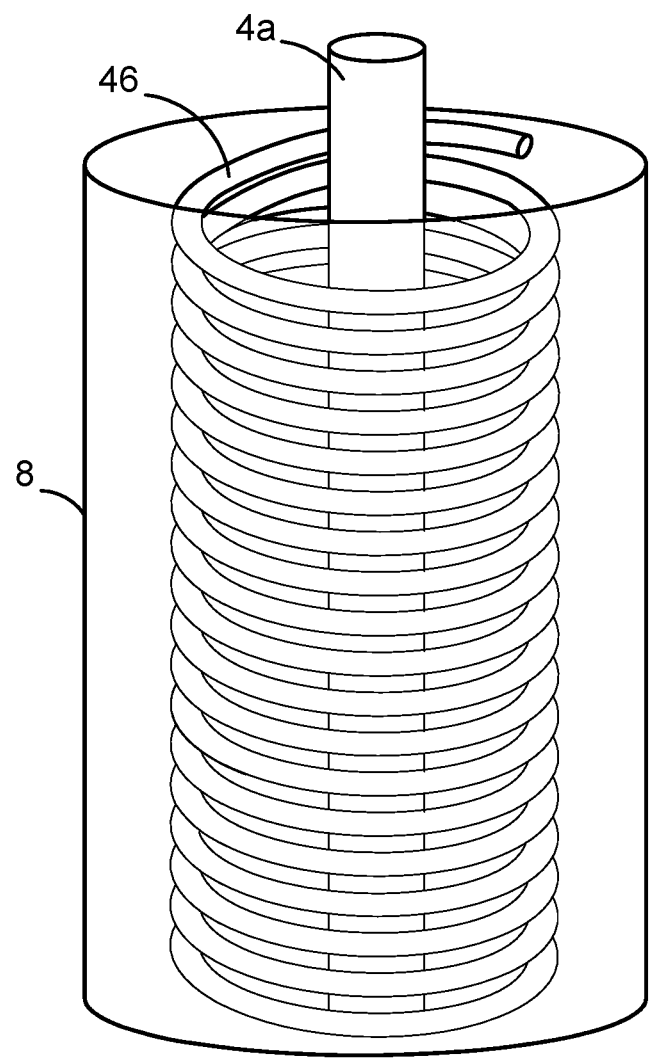
FIG. 7 is a diagram representing an isometric view of an optical impedance sensor having a spiral receiving optical fiber for use in a reservoir having a small depth, such as at a tip of a wing fuel tank.

In conjunction with the installation of a tall sensor in a fuel tank compartment near the root of the wing, a short sensor may be installed in a fuel tank compartment at the tip of the wing. Despite the short length of this sensor, the accuracy requirement is still 1%. FIG. 7 is a diagram representing an isometric view of portions (the total internal reflection optical fiber is not shown) of a differential optical fuel level having a spiral receiving optical fiber 46 for use in a reservoir having a small depth, such as at a tip of a wing fuel tank. The spiral receiving optical fiber 46 is placed inside a meniscus tube 8, wrapped around a central omni-directional side-emitting optical fiber 4a, to increase optical power pickup per unit sensor length.

Any one of the above-described differential optical fuel level sensors may be installed in a fuel tank onboard an airplane along with a densitometer. The fuel level and fuel density data and known geometry of the fuel tank can then be used to compute the estimated quantity (i.e., mass) of fuel in the fuel tank. (In order to measure the mass of the fuel for engine consumption and range calculation, the system can use measurements of fuel level and fuel density.) In addition, an airplane can be retrofit by removing existing electrical fuel level sensors and installing optical fuel level sensors in their place. In accordance with one fuel level sensor configuration, the locations of the respective sensors in the wing tank and the center tank of an airplane dictate the sensor height and therefore fiber sensor length. In the baseline configuration there would be a one-to-one replacement of each electrical sensor by an optical sensor. The double-shielded electrical wiring for the electrical sensor will be replaced by lightweight optical fiber, eliminating weight from the wiring and supporting brackets, and eliminating electromagnetic effects from lightning, shorting, fraying of electrical wiring. The use of optical fibers instead of electrical wires also eliminates any safety hazards due to electrical fault conditions. Although glass fiber can be used, plastic optical fiber is more flexible and more forgiving for installation in the very tight space of an airplane fuel tank.

Figure 8:
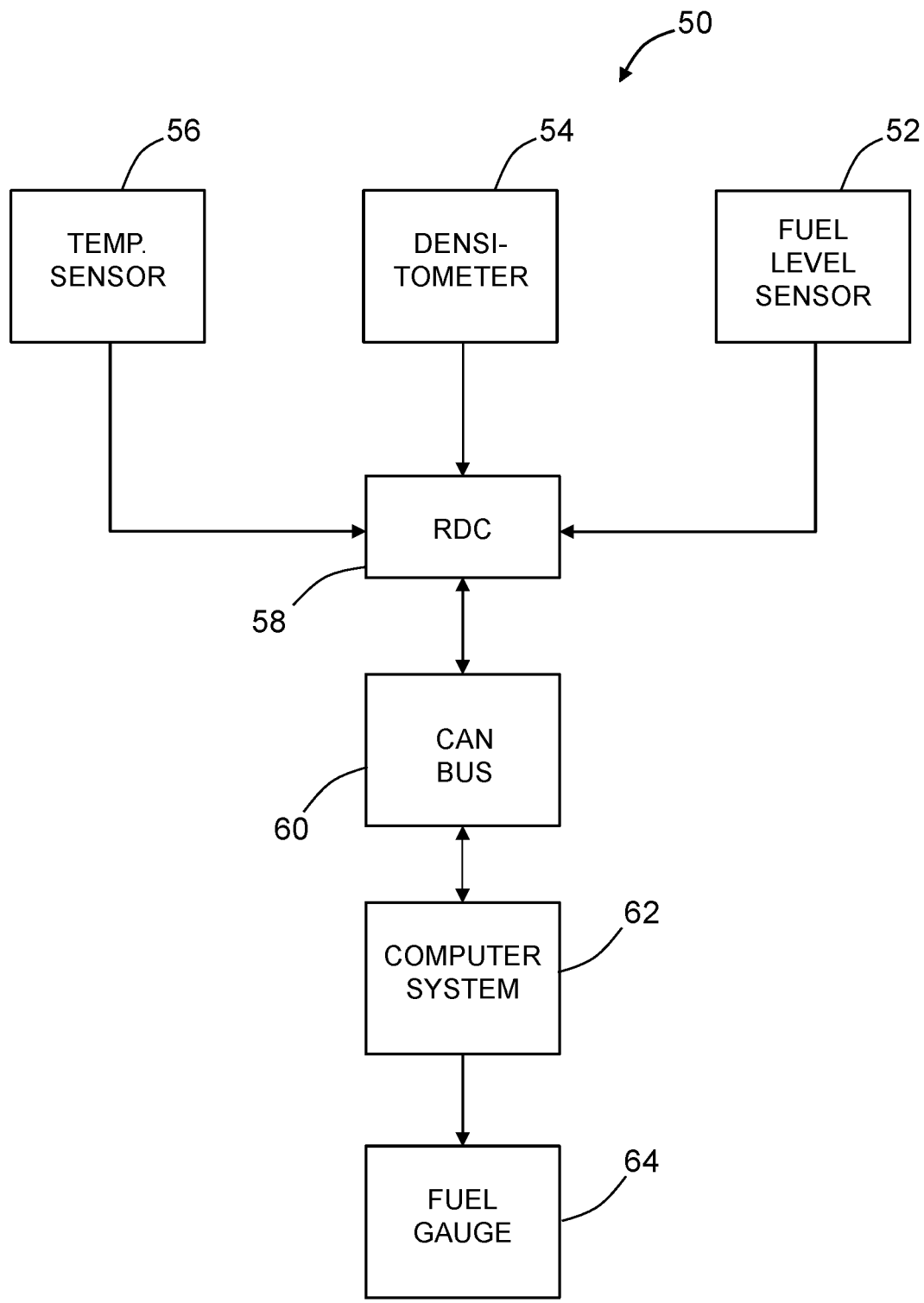
FIG. 8 is a block diagram identifying some components of a system for providing a pilot with an indication of the estimated quantity of fuel remaining in the fuel tank of an airplane.

FIG. 8 is a block diagram representing components of a system for measuring a quantity of fuel in a fuel tank in accordance with one embodiment. The system comprises a fuel level sensor 52 (of a type described above) that outputs electrical signals representing the level of fuel in a fuel tank, a densitometer 54 that outputs electrical signals representing the density of the fuel in the fuel tank and a temperature sensor 56 that outputs electrical signals representing the temperature of the fuel in the fuel tank. Each of these sensors may be incorporated in a respective line replaceable unit (LRU). These LRUs are connected to a remote data concentrator (RDC) 58.

In accordance with one implementation, the RDC 58 is connected to a computer system 62 (e.g., a fuel quantity processing unit) by way of a multi-master serial bus known as a CAN bus 60. For this purpose, the RDC 58 and the computer system 62 may each incorporate a controller and a transceiver of the type used in a controller area network (CAN). Such a CAN controller and CAN transceiver are referred to herein as a "CAN node". The RDC 58 has different dedicated analog circuits to separately measure the temperature, density, and level of the fuel. The analog values of these parameters are converted to digital values, packed in a data field and transmitted via the CAN bus 60 to the computer system 62. Note that ARINC 845 CAN bus is just an example of a simple avionic digital data bus that can be used and that any other digital data bus such as ARINC 425 or ARINC 664 can be used as well.

In accordance with the CAN communications protocol, each CAN node is able to send and receive messages, but not simultaneously. A message or frame consists primarily of an identifier, which represents the priority of the message, and a number of data bytes. The message is transmitted serially onto the CAN bus 60 by the CAN transceiver and may be received by all CAN nodes. Each CAN node connected to CAN bus 60 waits for a prescribed period of inactivity before attempting to send a message. If there is a collision (i.e., if two nodes try to send messages at the same time), the collision is resolved through a bit-wise arbitration, based on a preprogrammed priority of each message in the identifier field of the message. The message that contains the highest priority identifier always wins bus access.

The sensor data acquired by fuel level sensor 52, densitometer 54 and temperature sensor 56 is formatted in accordance with the CAN communications protocol to form CAN messages, which are broadcast onto the CAN bus 60 and received by the computer system 62. The computer system 62 is configured to estimate the mass of fuel remaining in the fuel tank (or compartment thereof) based on the measured fuel density, the known geometry of the fuel tank (or compartment thereof) and the measured fuel level h. For example, the volume of fuel remaining can be computed based on the known geometry and measured fuel level, and then the mass of fuel remaining will be equal to the product of volume and density. An electrical signal representing the estimated mass of remaining fuel is output from the computer system 62 to a fuel gauge 64. The fuel gauge 64 may take the form of a display device having a display processor programmed to display the measurement results (e.g., the fuel level or the fuel quantity) graphically and/or alphanumerically on a display screen.

In accordance with one proposed implementation, a differential optical fuel level sensor is installed in a compartment of a fuel tank. The optical source is in the form of a transmit integrated circuit connected to a transmit optical subassembly (comprising a laser or LED). Each optical detector is in the form of a receive integrated circuit connected to a receive optical subassembly (comprising a photodiode). The magnitude of the fuel level signals output by the differential optical fuel level sensor increases monotonically with increasing intensity of light emitted from the end of the side-receiving optical fiber 6. The computer system 62 may be a dedicated microprocessor or a general-purpose computer configured to perform differential processing of the signals representing the respective output optical powers S and R. This differential processing removes the undesirable effects of any common-mode intensity variations. The results of the differential processing are then used to calculate the measured level (i.e., height) of the fuel by using a look-up table, a calibration curve, or by solving equations, as appropriate.

The computer system 62 may be a computer or part of a flight control system located on an airplane. In identifying the amount of fuel present in an irregular-shaped fuel tank, the computer system 62 may execute various routines to calculate the amount of fuel present based on optical power data received from multiple differential optical fuel level sensors appropriately placed in various compartments of the fuel tank. The fuel information processing software may include routines that take into account the shape of the fuel tank to determine the amount of fuel remaining in the fuel tank. The fuel information processing software may further include routines for calibrating processes to form a baseline before a first use or to maintain accuracy of fuel readings. The readings provided by the computer system 62 to the fuel gauge 64 may be integrated or averaged before presentation and may be provided at different time intervals.

The passive differential optical liquid level sensors disclosed herein use a single transmit probe and harvest the otherwise-wasted optical energy at the bottom end of the transmit probe as a reference signal. That reference signal is guided out of the fuel tank by a jacketed optical fiber with total internal reflection which is placed in the fuel in the vicinity of transmit and receive probes and acts as a reference probe. Thus the optical fiber inside the reference probe is isolated from the fuel. The reference signal experiences all common-mode intensity variations caused by LED aging, fiber aging, waveguide aging, fuel gunk, etc., but is not influenced by fuel level. The sensing signal experiences all of the same common-mode intensity variations, but also varies as a function of the fuel level.

While differential optical liquid level sensors have been described with reference to various embodiments, it will be understood by those skilled in the art that various changes may be made and equivalents may be substituted for elements thereof without departing from the teachings herein. In addition, many modifications may be made to adapt the concepts and reductions to practice disclosed herein to a particular situation. Accordingly, it is intended that the subject matter covered by the claims not be limited to the disclosed embodiments.

The embodiments disclosed above use one or more computing systems. As used in the claims, the term "computing system" comprises one or more of the following: a computer, a processor, a controller, a central processing unit, a microcontroller, a reduced instruction set computer processor, an ASIC, a programmable logic circuit, an FPGA, a digital signal processor, and/or any other circuit or processing device capable of executing the functions described herein. For example, a computing system may comprise multiple microcontrollers or multiple processors which communicate via a network or bus. As used herein, the terms "computer" and "processor" both refer to devices having a processing unit (e.g., a central processing unit) and some form of memory (i.e., computer-readable medium) for storing a program which is readable by the processing unit.

The methods described herein may be encoded as executable instructions embodied in a non-transitory tangible computer-readable storage medium, including, without limitation, a storage device and/or a memory device. Such instructions, when executed by a processing or computing system, cause the system device to perform at least a portion of the methods described herein.

The process claims set forth hereinafter should not be construed to require that the steps recited therein be performed in alphabetical order (any alphabetical ordering in the claims is used solely for the purpose of referencing previously recited steps) or in the order in which they are recited unless the claim language explicitly specifies or states conditions indicating a particular order in which some or all of those steps are performed. Nor should the process claims be construed to exclude any portions of two or more steps being performed concurrently or alternatingly unless the claim language explicitly states a condition that precludes such an interpretation.

The invention claimed is:

1. A system for measuring a level of liquid in a reservoir, comprising:
   an optical source configured to convert input electrical power to output light;
   a first optical detector configured to convert impinging light into electrical signals having an amplitude which is a function of a first optical power of the light impinging on the first optical detector;
   a second optical detector configured to convert impinging light into electrical signals having an amplitude which is a function of a second optical power of the light impinging on the second optical detector;
   a side-emitting optical fiber positioned in the reservoir and having one end optically coupled to the optical source and having another end;
   a side-receiving optical fiber that is positioned parallel to and at a distance from the side-emitting optical fiber in the reservoir and has one end optically coupled to the first optical detector;
   a total internal reflection optical fiber positioned in the reservoir and having one end optically coupled to the second optical detector and another end optically coupled to the another end of the side-emitting optical fiber; and
   a computer system configured to subtract a first electrical signal output by the first optical detector from a second electrical signal output by the second optical detector and then output a third electrical signal representing a height of an air/liquid interface in the reservoir, wherein:
   the first electrical signal represents sensing optical power output from the one end of the side-receiving optical fiber in response to output of light by the optical source;
   the second electrical signal represents reference optical power output from the one end of the total internal reflection optical fiber in response to the output of light by the optical source; and
   the third electrical signal is a function of a difference of the first and second electrical signals.

2. The system as recited in claim 1, further comprising a display device electrically coupled to the computing system, wherein the computing system is further configured to execute the following operations:

storing data representing a geometry of the reservoir;
receiving data representing a measurement of a density of the liquid in the reservoir;
calculating a mass of liquid remaining in the reservoir based on the geometry of the reservoir, the density of the liquid and the estimated level of liquid; and
outputting an electrical signal representing the calculated mass of liquid in the reservoir to the display device.

3. The system as recited in claim 1, wherein the side-emitting optical fiber comprises a first side window and the side-receiving optical fiber comprises a second side window, the side-emitting optical fiber is configured to side-emit light through the first side window, and the side-emitting optical fiber and side-receiving optical fiber are arranged so that the side-emitted light is directed toward the second side window.

4. The system as recited in claim 1, further comprising an optical waveguide that bridges the another ends of the side-emitting optical fiber and the total internal reflection optical fiber.

5. The system as recited in claim 1, wherein the reservoir is a fuel tank of an airplane.

6. A fuel storage system comprising:
a fuel tank having a geometry that defines a volume;
a meniscus tube disposed within the volume defined by the geometry of the fuel tank;
a first side-emitting optical fiber having one end and another end;
a side-receiving optical fiber that is positioned parallel to and at a distance from the first side-emitting optical fiber and has one end and another end; and
a first total internal reflection optical fiber having one end and having another end optically coupled to the another end of the first side-emitting optical fiber,
wherein the first side-emitting optical fiber, the side-receiving optical fiber and the first total internal reflection optical fiber are disposed within the meniscus tube,
the fuel storage system further comprising:
an optical source configured to convert input electrical power to output light, wherein the optical source is optically coupled to the one end of the first side-emitting optical fiber;
a first optical detector configured to convert impinging light into electrical signals having an amplitude which is a function of a first optical power of the light impinging on the first optical detector, wherein the first optical detector is optically coupled to the one end of the side-receiving optical fiber;
a second optical detector configured to convert impinging light into electrical signals having an amplitude which is a function of a second optical power of the light impinging on the second optical detector, wherein the second optical detector is optically coupled to the one end of the first total internal reflection optical fiber; and
a computer system configured to subtract a first electrical signal output by the first optical detector from a second electrical signal output by the second optical detector and then output a third electrical signal representing an estimated level of fuel in the reservoir, wherein:
the first electrical signal represents sensing optical power output from the one end of the side-receiving optical fiber in response to output of light by the optical source;
the second electrical signal represents reference optical power output from the one end of the total internal reflection optical fiber in response to the output of light by the optical source; and
the third electrical signal is a function of a difference of the first and second electrical signals.

7. The system as recited in claim 6, further comprising:
a display device electrically coupled to the computing system; and
a densitometer located in the fuel tank and configured to measure a density of fuel in the fuel tank,
wherein the computing system is further configured to execute the following operations:
storing data representing the geometry of the fuel tank;
receiving data from the densitometer representing a measurement of a density of the fuel in the fuel tank;
calculating a mass of fuel remaining in the fuel tank based on the geometry of the fuel tank, the density of the fuel and the estimated level of fuel; and
outputting an electrical signal representing the calculated mass of fuel in the fuel tank to the display device.

8. The system as recited in claim 6, wherein the first side-emitting optical fiber comprises a first side window and the side-receiving optical fiber comprises a second side window, the first side-emitting optical fiber is configured to side-emit light through the first side window, and the first side-emitting optical fiber and side-receiving optical fiber are arranged so that the side-emitted light is directed toward the second side window.

9. The system as recited in claim 6, further comprising an optical waveguide that bridges the another ends of the side-emitting optical fiber and the total internal reflection optical fiber.

10. A method for measuring a height of liquid in a reservoir, comprising:
optically coupling one end of a side-emitting optical fiber to one end of a total internal reflection optical fiber;
placing the optically coupled side-emitting and total internal reflection optical fibers in the reservoir;
placing a side-receiving optical fiber in the reservoir at a location whereat the side-emitting optical fiber and side-receiving optical fiber are mutually parallel and separated by a distance;
outputting light from an optical source;
guiding the outputted light into another end of the side-emitting optical fiber;
side-emitting at least some of the light propagating in the side-emitting optical fiber toward the side-receiving optical fiber;
guiding at least some of the light received by the side-receiving optical fiber onto a first optical detector;
guiding at least some of the light received by the total internal reflection optical fiber onto a second optical detector;
converting light that impinges on the first optical detector into first electrical signals;
converting light that impinges on the second optical detector into second electrical signals; and
estimating an estimated level of liquid in the reservoir based on a difference of the first and second electrical signals, wherein:
the first electrical signals represent sensing optical power output from the one end of the side-receiving optical fiber in response to output of light by the optical source;
the second electrical signal represents reference optical power output from the one end of the total internal reflection optical fiber in response to the output of light by the optical source; and
estimating the estimated level of liquid in the reservoir comprises outputting from a computer system a third electrical signal that is a function of a difference of the first and second electrical signals.

11. The method as recited in claim 10, further comprising: storing data representing a geometry of the reservoir; measuring a density of the liquid in the reservoir; calculating a mass of liquid remaining in the reservoir based on the geometry of the reservoir, the density of the liquid and the estimated level of liquid; and displaying a gauge that indicates the calculated mass of liquid in the reservoir.

12. The method as recited in claim 11, further comprising acquiring data samples by filling the reservoir with various levels of liquid at different times and then recording the resulting differences between respective sets of first and second electrical signals output by the first and second optical detectors respectively.

13. The method as recited in claim 12, further comprising: generating digital calibration data representing the levels of liquid versus the associated differences for each level; and recording that digital calibration data in a look-up table stored in a non-transitory tangible computer-readable storage medium.

14. The method as recited in claim 13, further comprising: deriving a linear equation that fits the digital calibration data; and using the linear equation to interpolate between two stored values in the look-up table when a difference of the first and second electrical signals represents a value between those two stored values.

15. The method as recited in claim 10, wherein the liquid is fuel and the reservoir is a fuel tank onboard an airplane.

* * * * *